(12) United States Patent
Schwarz et al.

(10) Patent No.: US 7,407,551 B2
(45) Date of Patent: Aug. 5, 2008

(54) MECHANICAL AND ACOUSTICAL SUSPENSION COATING OF MEDICAL IMPLANTS

(75) Inventors: Marlene C. Schwarz, Auburndale, MA (US); Stanley Tocker, Wilmington, DE (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 10/699,771

(22) Filed: Nov. 4, 2003

(65) Prior Publication Data

US 2004/0089230 A1 May 13, 2004

Related U.S. Application Data

(63) Continuation of application No. 10/084,868, filed on Mar. 1, 2002, now Pat. No. 6,730,349, which is a continuation-in-part of application No. 09/804,030, filed on Mar. 13, 2001, now Pat. No. 6,607,598, which is a continuation-in-part of application No. 09/551,614, filed on Apr. 17, 2000, now Pat. No. 6,368,658, which is a continuation-in-part of application No. 09/293,994, filed on Apr. 19, 1999, now abandoned.

(51) Int. Cl.
*B05B 17/00* (2006.01)

(52) U.S. Cl. ................................. 118/303; 118/DIG. 5

(58) Field of Classification Search .................. 118/303, 118/DIG. 5, 57, 417, 106; 427/213, 2.15, 427/2.1, 459, 184, 214, 185; 422/127, 128; 604/265

See application file for complete search history.

(56) References Cited

U.S. PATENT DOCUMENTS

| 2,648,609 A | 8/1953 | Wurster | 99/116 |
|---|---|---|---|
| 2,799,241 A | 7/1957 | Wurster | 118/24 |
| 3,089,824 A | 5/1963 | Wurster | 167/82 |
| 3,253,944 A | 5/1966 | Wurster | 117/100 |
| 3,431,138 A | 3/1969 | Zingerman et al. | |
| 3,567,485 A | 3/1971 | Lemelson | 117/21 |
| 3,759,218 A * | 9/1973 | Korstvedt | 118/18 |
| 3,846,566 A * | 11/1974 | Blomstrom | 426/250 |
| 4,000,338 A | 12/1976 | Burdin | 427/184 |
| 4,180,560 A | 12/1979 | Katz et al. | 424/21 |
| 4,182,871 A | 1/1980 | Moller | |
| 4,224,090 A * | 9/1980 | Garner | |
| 4,241,102 A * | 12/1980 | McKinley et al. | |
| 4,312,893 A | 1/1982 | Futter | 427/3 |

(Continued)

FOREIGN PATENT DOCUMENTS

| DE | 33 23 418 A | 1/1985 |
|---|---|---|
| EP | 0 627 266 A | 12/1994 |
| EP | 1 166 895 A1 | 1/2002 |
| WO | WO 96/17692 A | 6/1996 |

*Primary Examiner*—Brenda A. Lamb
(74) *Attorney, Agent, or Firm*—Kenyon & Kenyon LLP

(57) ABSTRACT

The present invention has several plausible embodiments. In one embodiment an apparatus for coating a medical device is provided. This apparatus includes a coating chamber, a vibrating structure within the coating chamber the vibrating structure capable of suspending a medical device positioned in the coating chamber, and a coating source, the coating source positioned to introduce coating into the coating chamber. In another embodiment a method of coating a medical device is provided. This method includes moving a medical device into a predetermined coating area, vibrating a structure below the medical device, the vibration of the structure forcing the medical device away from the vibrating structure, and coating at least a portion of the medical device that has moved away from the vibrating structure.

10 Claims, 9 Drawing Sheets

U.S. PATENT DOCUMENTS

| | | | |
|---|---|---|---|
| 4,320,089 A | 3/1982 | Hüttlin | |
| 4,349,498 A | 9/1982 | Ellis et al. | 264/81 |
| 4,428,973 A | 1/1984 | Horner et al. | |
| 4,432,933 A | 2/1984 | Teitel et al. | 376/152 |
| 4,442,003 A * | 4/1984 | Holt | |
| 4,447,251 A * | 5/1984 | Dunn et al. | 65/142 |
| 4,495,215 A | 1/1985 | Barnert et al. | |
| 4,529,614 A | 7/1985 | Burns | 427/2 |
| 4,533,255 A * | 8/1985 | Gronholz et al. | 366/108 |
| 4,535,006 A | 8/1985 | Naunapper et al. | |
| 4,554,887 A | 11/1985 | Yoakam et al. | 118/666 |
| 4,592,920 A | 6/1986 | Murtfeldt | 427/2 |
| 4,633,804 A | 1/1987 | Arii | |
| 4,656,056 A | 4/1987 | Leuenberger | |
| 4,666,704 A | 5/1987 | Shalati et al. | 424/19 |
| 4,684,523 A | 8/1987 | Ferrero | 424/441 |
| 4,724,794 A | 2/1988 | Itoh | |
| 4,740,390 A | 4/1988 | Külling | |
| 4,745,011 A * | 5/1988 | Fukuta et al. | |
| 4,760,815 A | 8/1988 | Rockx | |
| 4,828,882 A | 5/1989 | Tsezos et al. | |
| 4,848,673 A | 7/1989 | Masuda et al. | |
| 4,858,552 A | 8/1989 | Glatt et al. | |
| 4,883,004 A | 11/1989 | Hansen | |
| 4,886,701 A | 12/1989 | Ehnert et al. | |
| 4,895,733 A | 1/1990 | Imanidis et al. | |
| 4,919,973 A | 4/1990 | Alkan et al. | |
| 4,951,472 A | 8/1990 | Hansen et al. | |
| 4,994,013 A | 2/1991 | Suthanthiran et al. | 600/8 |
| 5,015,501 A | 5/1991 | Johnson | 427/212 |
| 5,017,401 A | 5/1991 | van Drunen | |
| 5,038,709 A | 8/1991 | Yamada et al. | 118/666 |
| 5,123,373 A * | 6/1992 | Iyer et al. | 118/612 |
| 5,132,142 A | 7/1992 | Jones et al. | |
| 5,133,137 A | 7/1992 | Petersen | |
| 5,158,804 A | 10/1992 | Alkan et al. | |
| 5,192,308 A | 3/1993 | Ostapchenko | 623/1 |
| 5,221,698 A | 6/1993 | Amidon et al. | 523/122 |
| 5,223,088 A | 6/1993 | Hansen | |
| 5,227,018 A | 7/1993 | Bro et al. | |
| 5,236,503 A | 8/1993 | Jones | |
| 5,248,387 A | 9/1993 | Hansen | |
| 5,272,012 A * | 12/1993 | Opolski | |
| 5,284,678 A | 2/1994 | Hirschfeld et al. | |
| 5,296,265 A | 3/1994 | Okuma et al. | |
| 5,302,201 A | 4/1994 | Lücke | 118/19 |
| 5,328,270 A | 7/1994 | Crawford et al. | |
| 5,328,720 A | 7/1994 | Emken et al. | 427/2.3 |
| 5,338,553 A | 8/1994 | Johnson et al. | |
| 5,405,309 A | 4/1995 | Carden, Jr. | 600/3 |
| 5,435,980 A | 7/1995 | Felsvang et al. | |
| 5,437,889 A | 8/1995 | Jones | |
| 5,447,966 A | 9/1995 | Hermes et al. | 523/113 |
| 5,464,650 A * | 11/1995 | Berg et al. | 427/2.3 |
| 5,470,387 A | 11/1995 | Liborius | |
| 5,495,418 A | 2/1996 | Latini et al. | 364/468 |
| 5,507,868 A | 4/1996 | Takei et al. | 118/19 |
| 5,518,180 A | 5/1996 | Svendsen | |
| 5,527,171 A | 6/1996 | Soerensen | |
| 5,527,533 A * | 6/1996 | Tso et al. | 424/422 |
| 5,590,961 A | 1/1997 | Rasmussen | |
| 5,593,715 A | 1/1997 | Christensen | |
| 5,596,817 A | 1/1997 | Hansen | |
| 5,611,151 A | 3/1997 | Jacob | |
| 5,624,411 A | 4/1997 | Tuch | 604/265 |
| 5,632,100 A | 5/1997 | Hansen | |
| 5,632,102 A | 5/1997 | Luy et al. | |
| 5,648,118 A | 7/1997 | Liborius | |
| 5,656,325 A | 8/1997 | Wallace | |
| 5,679,400 A | 10/1997 | Tuch | 427/2.14 |
| 5,679,402 A | 10/1997 | Lee | 427/127 |
| 5,686,045 A * | 11/1997 | Carter | 422/20 |
| 5,695,701 A | 12/1997 | Funder et al. | |
| 5,817,280 A | 10/1998 | Larsen et al. | |
| 5,837,008 A | 11/1998 | Berg et al. | 623/1 |
| 5,837,284 A | 11/1998 | Mehta et al. | 424/459 |
| 5,840,360 A | 11/1998 | Larsen | |
| 5,855,915 A | 1/1999 | Pinkus | 424/486 |
| 5,870,783 A | 2/1999 | Stoll et al. | |
| 5,876,750 A | 3/1999 | Jao et al. | 424/457 |
| 5,968,575 A | 10/1999 | Rasmussen | |
| 5,972,985 A | 10/1999 | Thomas et al. | 514/400 |
| 5,980,882 A | 11/1999 | Eichman | 428/78.12 |
| 6,046,277 A | 4/2000 | Kolter et al. | 525/205 |
| 6,056,993 A * | 5/2000 | Leidner et al. | 427/2.25 |
| 6,058,624 A | 5/2000 | Bach et al. | |
| 6,098,895 A | 8/2000 | Walzel et al. | |
| 6,143,431 A | 11/2000 | Webster | 428/669 |
| 6,149,785 A | 11/2000 | Makowiecki et al. | 204/298.28 |
| 6,151,798 A | 11/2000 | Petersen | |
| 6,171,649 B1 | 1/2001 | Keener et al. | |
| 6,174,329 B1 | 1/2001 | Callol et al. | 623/1.34 |
| 6,209,479 B1 | 4/2001 | Walter et al. | |
| 6,312,521 B1 | 11/2001 | Lee et al. | |
| 6,338,438 B1 | 1/2002 | Walzel et al. | |
| 6,364,903 B2 | 4/2002 | Tseng et al. | |
| 6,364,948 B1 | 4/2002 | Austin et al. | |
| 6,383,553 B1 | 5/2002 | Tondar et al. | |
| 6,395,326 B1 | 5/2002 | Castro et al. | |
| 6,457,657 B1 | 10/2002 | Nielsen | |
| 6,461,672 B1 | 10/2002 | Kosola et al. | |
| 6,497,911 B1 | 12/2002 | Hansen et al. | |
| 2001/0022988 A1 | 9/2001 | Schwarz et al. | |
| 2001/0055648 A1 | 12/2001 | Lee et al. | |

* cited by examiner

MECHANICAL AND ACOUSTICAL SUSPENSION COATING OF MEDICAL IMPLANTS

This application is a continuation of application Ser. No. 10/084,868, filed Mar. 1, 2002 now U.S. Pat. No. 6,730,349, which is a continuation-in-part of application Ser. No. 09/804,040, filed Mar. 13, 2001 now U.S. Pat. No. 6,607,598, which is a continuation-in-part of application Ser. No. 09/551,614, filed Apr. 17, 2000, now U.S. Pat. No. 6,368,658, which is a continuation-in-part of application Ser. No. 09/293,994, filed Apr. 19, 1999, now abandoned.

FIELD OF THE INVENTION

The present invention relates to coating medical implants. More specifically, the present invention regards coating medical implants that are agitated or moved due to the vibration of a vibrating structure.

BACKGROUND OF THE INVENTION

It is often beneficial to coat medical devices so that the surfaces of such devices have desired properties or effects. For example, it is useful to coat medical devices to provide for the localized delivery of therapeutic agents to target locations within the body, such as to treat localized disease (e.g., heart disease) or occluded body lumens. Such localized drug delivery avoids the problems of systemic drug administration, which may be accompanied by unwanted effects on parts of the body which are not to be treated, or because treatment of the afflicted part of the body requires a high concentration of therapeutic agent that may not be achievable by systemic administration. Localized drug delivery is achieved, for example, by coating balloon catheters, stents and the like with a therapeutic agent. The coating on medical devices may provide for controlled release, which includes long-term or sustained release, of a bioactive material.

Aside from facilitating localized drug delivery, medical devices are coated with materials to provide beneficial surface properties. For example, medical devices are often coated with radiopaque materials to allow for fluoroscopic visualization during placement in the body. It is also useful to coat certain devices to achieve enhanced biocompatibility and to improve surface properties such as lubriciousness.

Conventionally, coatings have been applied to medical devices by processes such as dipping, spraying, vapor deposition, plasma polymerization, and electro-deposition. Although these processes have been used to produce satisfactory coatings, there are numerous potential drawbacks associated therewith. For example, it is often difficult to achieve coatings of uniform thickness, both on individual parts and on batches of parts. Also, many of these conventional coating processes require that the coated part be held during coating, resulting in defects such as bare spots where the part was held and thus requiring subsequent coating steps.

There is, therefore, a need for a cost-effective method of coating medical devices that results in uniform, defect-free coatings and uniform drug doses per unit device. The method would allow for a multiple stage coating in order to apply a bioactive material that may be environmentally sensitive, e.g., due to heat and light (including ultra-violet) exposure and due to degradation of the bioactive material due to process-related forces (e.g., shear). The method would, thus, allow for better control of the sensitivity of the bioactive material and reduce any potential degradation due to environmental issues. The method would also reduce variations in the coating properties.

SUMMARY OF THE INVENTION

The present invention has several plausible embodiments. In one embodiment an apparatus for coating a medical device is provided. This apparatus includes a coating chamber; a vibrating structure within the coating chamber the vibrating structure capable of suspending a medical device positioned in the coating chamber, and a coating source, the coating source positioned to introduce coating into the coating chamber.

In another embodiment a method of coating a medical device is provided. This method includes moving a medical device into a predetermined coating area, vibrating a structure below the medical device, the vibration of the structure forcing the medical device away from the vibrating structure, and coating at least a portion of the medical device that has moved away from the vibrating structure.

In another embodiment a medical device is provided. This medical device may have been manufactured by moving the medical device into a predetermined coating area, vibrating a structure below the medical device, the vibration of the structure forcing the medical device away from the vibrating structure, and coating at least a portion of the medical device that has moved away from the vibrating structure.

DETAILED DESCRIPTION

Figure 1:
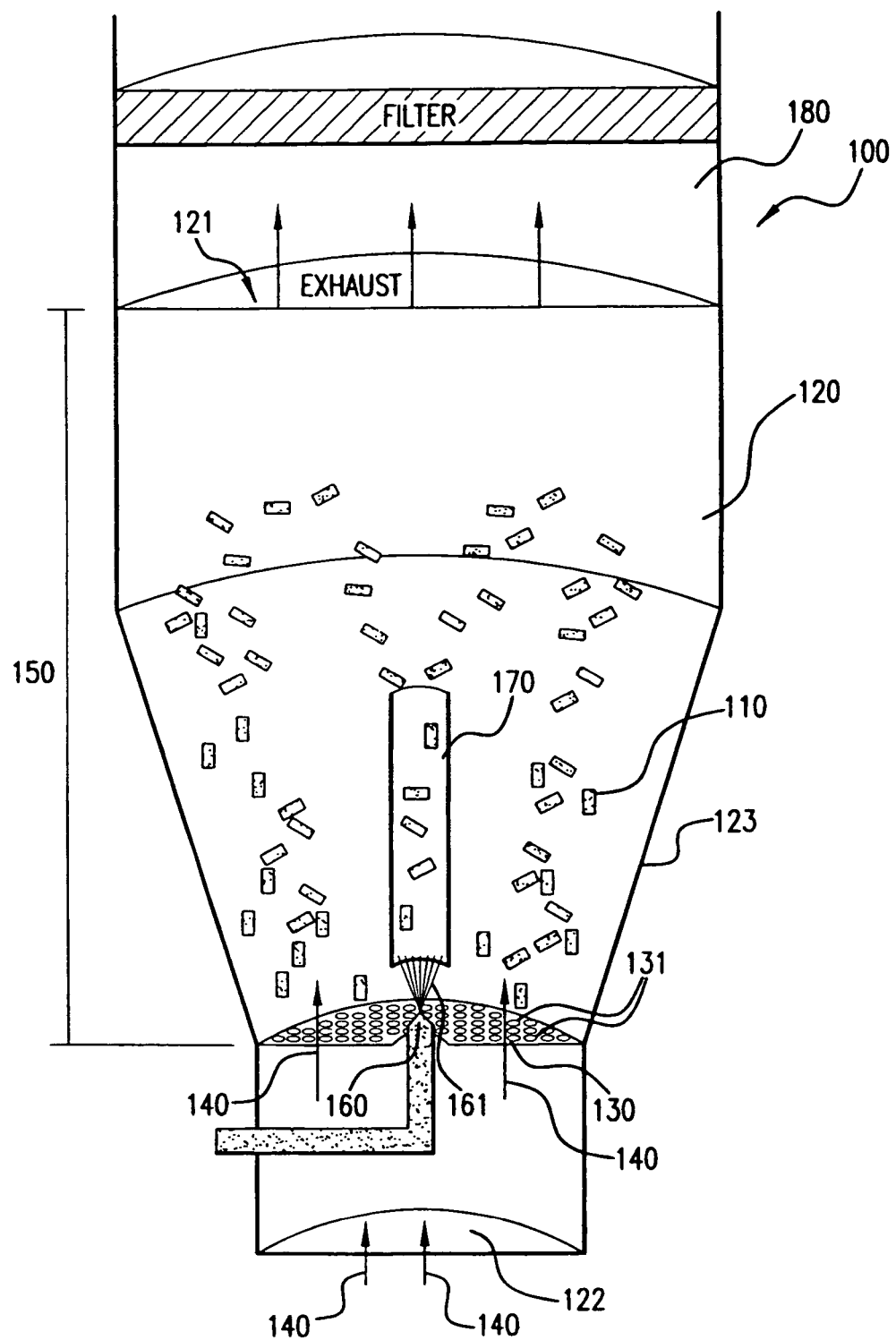
FIG. 1 is a cross-sectional view of an apparatus for coating medical devices in accordance with a first embodiment of the present invention.

The present invention provides methods for coating medical devices and devices thereby produced. By using air suspension or mechanical vibration to coat medical devices, the methods of the present invention result in coatings having minimal defects and uniform thicknesses and mechanical properties. Further, the methods of the present invention are time efficient and cost effective because they facilitate the uniform coating of numerous medical devices in a single batch.

Whereas the present invention allows multiple medical devices to be coated as a batch, the present invention is not limited to only coating medical devices in batches, i.e., coating a group of devices in one batch process followed by coating a second group of devices in a second batch process.

The methods and apparatus of the present invention can be utilized to continuously run medical devices through the apparatus such that the process does not have to be started and stopped for coating the medical devices in batches. The medical devices can be run through a continuous process.

In embodiments of the present invention, single or multiple coating materials are applied to medical devices by suspending the medical device and, then, coating at least a portion of the medical device. The means for suspending the medical device can include mechanical or acoustical structures. An air stream can be incorporated into the suspending structure. As used herein, "air stream" refers to a stream of any suitable gas, such as air, nitrogen, argon and combinations thereof. The air stream is said to be "substantially devoid of suspending particles", i.e., particles are not utilized to suspend the medical devices within the air stream. Any non-coating particles (i.e., particles that do not become at least partially part of the coating materials) that may be present in the air stream do not materially provide for suspending the medical devices. Particles might be added to the air stream to enhance the coating process, e.g., a polishing media and/or electrostatic inhibitors in low ratios, however, these added particles are not used to suspend the articles to be coated.

Thus, the air stream, since it is substantially devoid of suspending particles and only requires the air itself in the air stream to suspend the medical devices, may be termed a homogenous suspending air stream. As used herein, "suspending" the medical device shall refer to a process whereby the medical device is situated within the flow of an air stream and may be moving within the air stream while unsupported by any external means. "Suspending" can also refer to vibrating a structure below the medical device at a given frequency in order to suspend the device above the vibrating structure.

The medical devices used in conjunction with the present invention include any device or implant amenable to the coating processes described herein. The medical device, or portion of the medical device, to be coated or surface modified may be made of metal, polymers, ceramics, composites or combinations thereof, and for example, may be coated with one or more of these materials. Whereas the present invention is described herein with specific reference to a vascular stent, other medical devices within the scope of the present invention include any devices which are used, at least in part, to penetrate the body of a patient. Examples include implantable devices such as catheters, needle injection catheters, blood clot filters, vascular grafts, stent grafts, biliary stents, colonic stents, bronchial/pulmonary stents, esophageal stents, ureteral stents, aneurysm filling coils and other coiled coil devices, trans myocardial revascularization ("TMR") devices, percutaneous myocardial revascularization ("PMR") devices etc., as are known in the art, as well as devices such as hypodermic needles, soft tissue clips, holding devices, and other types of medically useful needles and closures. Any exposed surface of these medical devices may be coated with the methods and apparatuses of the present invention including, for example, the inside exposed surface and the outside exposed surface of a tubular medical device that is open at both ends.

The coating materials used in conjunction with the present invention are any desired, suitable substances. In some embodiments, the coating materials comprise therapeutic agents, applied to the medical devices alone or in combination with solvents in which the therapeutic agents are at least partially soluble or dispersible or emulsified, and/or in combination with polymeric materials as solutions, dispersions, suspensions, lattices, etc. The terms "therapeutic," "therapeutic agents," and "drugs" are used interchangeably herein and include pharmaceutically active compounds, nucleic acids with and without carrier vectors such as lipids, compacting agents (such as histones), virus, polymers, proteins, and the like, with or without targeting sequences. The coating on the medical devices may provide for controlled release, which includes long-term or sustained release, of a bioactive material.

Specific examples of therapeutic or bioactive agents used in conjunction with the present invention include, for example, pharmaceutically active compounds, proteins, oligonucleotides, ribozymes, anti-sense genes, DNA compacting agents, gene/vector systems (i.e., anything that allows for the uptake and expression of nucleic acids), nucleic acids (including, for example, recombinant nucleic acids; naked DNA, cDNA, RNA; genomic DNA, cDNA or RNA in a non-infectious vector or in a viral vector which may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic polymers that are selected from a number of types depending on the desired application. For example, biologically active solutes include anti-thrombogenic agents such as heparin, heparin derivatives, urokinase, and PPACK (dextrophenylalanine proline arginine chloromethylketone); prostaglandins, prostacyclins/prostacyclin analogs; antioxidants such as probucol and retinoic acid; angiogenic and anti-angiogenic agents; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine, lipoxygenase inhibitors; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, colchicine, epothilones, endostatin, angiostatin, squalamine, and thymidine kinase inhibitors; L-arginine; antimicrobials such as triclosan, cephalosporins, aminoglycosides, and nitrofurantoin; anesthetic agents such as lidocaine, bupivacaine, and ropivacaine; nitric oxide (NO) donors such as linsidomine, molsidomine, NO-protein adducts, NO-polysaccharide adducts, polymeric or oligomeric NO adducts or chemical complexes; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, warfarin sodium, Dicumarol, aspirin, prostaglandin inhibitors, platelet inhibitors and tick antiplatelet factors; interleukins, interferons, and free radical scavengers; vascular cell growth promoters such as growth factors, growth factor receptor antagonists, transcriptional activators, and translational promotors; vascular cell growth inhibitors such as growth factor inhibitors (e.g., PDGF inhibitor—Trapidil), growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; Tyrosine kinase inhibitors, chymase inhibitors, e.g., Tranilast, ACE inhibitors, e.g., Enalapril, MMP inhibitors, (e.g., Ilomastat, Metastat), GP IIb/IIIa inhibitors (e.g., Integrilin, abciximab), serotonin antagonist, and 5-HT uptake inhibitors; cholesterol-lowering agents; vasodilating agents; agents which interfere with endogenous vascoactive mechanisms; survival genes which protect against cell death, such as anti-apoptotic Bcl-2 family factors and Akt kinase; and combinations thereof; and beta blockers. These and other compounds may be added to a coating solution, including a coating solution that includes a polymer, using similar methods and routinely tested as set forth in the specification.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides of the invention can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be incorporated into the polymer coating, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor and, platelet-derived endothelial growth factor, platelet-derived growth factor, tumor necrosis factor, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMPs are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Coating materials other than therapeutic agents include, for example, polymeric materials, sugars, waxes, and fats, applied alone or in combination with therapeutic agents, and monomers that are cross-linked or polymerized. Such coating materials are applied in the form of, for example, powders, solutions, dispersions, suspensions, and/or emulsions of one or more polymers, optionally in aqueous and/or organic solvents and combinations thereof or optionally as liquid melts including no solvents. When used with therapeutic agents, the polymeric materials are optionally applied simultaneously with, or in sequence to (either before or after), the therapeutic agents. Such polymeric materials employed as, for example, primer layers for enhancing subsequent coating applications (e.g., application of alkanethiols or sulfhydryl-group containing coating solutions to gold-plated devices to enhance adhesion of subsequent layers), layers to control the release of therapeutic agents (e.g., barrier diffusion polymers to sustain the release of therapeutic agents, such as hydrophobic polymers; thermal responsive polymers; pH-responsive polymers such as cellulose acetate phthalate or acrylate-based polymers, hydroxypropyl methylcellulose phthalate, and polyvinyl acetate phthalate), protective layers for underlying drug layers (e.g., impermeable sealant polymers such as ethylcellulose), biodegradable layers, biocompatible layers (e.g., layers comprising albumin or heparin as blood compatible biopolymers, with or without other hydrophilic biocompatible materials of synthetic or natural origin such as dextrans, cyclodextrins, polyethylene oxide, and polyvinyl pyrrolidone), layers to facilitate device delivery (e.g., hydrophilic polymers, such as polyvinyl pyrrolidone, polyvinyl alcohol, polyalkylene gylcol (i.e., for example, polyethylene glycol), or acrylate-based polymer/copolymer compositions to provide lubricious hydrophilic surfaces), drug matrix layers (i.e., layers that adhere to the medical device and have therapeutic agent incorporated therein or thereon for subsequent release into the body), and epoxies.

When used as a drug matrix layer for localized drug delivery, the polymer coatings of the present invention comprise any material capable of absorbing, adsorbing, entrapping, or otherwise holding the therapeutic agent to be delivered. The material is, for example, hydrophilic, hydrophobic, and/or biodegradable, and is preferably selected from the group consisting of polycarboxylic acids, cellulosic polymers, gelatin, polyvinylpyrrolidone, maleic anhydride polymers, polyamides, polyvinyl alcohols, polyethylene oxides, polylactic glycolic acid copolymers, glycosaminoglycans, polysaccharides, polyesters, polyurethanes, silicones, polyurea, polyacrylate, polyacrylic acid and copolymers, polyorthoesters, polyanhydrides, polycarbonates, polyethylene, polypropylenes, polylactic acids, polystyrene, natural and synthetic rubbers and elastomers such as polyisobutylene, polyisoprene, polybutadiene, including elastomeric copolymers, such as Kraton.RTM., styrene-isobutylene-styrene (SIBS) copolymers styrene-butadiene copolymers; polyglycolic acids, polycaprolactones, polyhydroxybutyrate valerates, polyacrylamides, polyethers, polysaccharides such as cellulose, starch, dextran and alginates; polypeptides and proteins including gelatin, collagen, albumin, fibrin; copolymers of vinyl monomers such as ethylene-vinyl acetate (EVA), polyvinyl ethers, polyvinyl aromatics; other materials such as cyclodextrins, hyaluronic acid and phosphoryicholines, and mixtures and copolymers thereof. Coatings from polymer dispersions such as polyurethane dispersions (BAYHDROL, etc.) and acrylic latex dispersions are also within the scope of the present invention. Preferred polymers include polyurethanes; polyacrylic acid as described in U.S. Pat. No. 5,091,205, the disclosure of which is incorporated herein by reference; and aqueous coating compositions comprising an aqueous dispersion or emulsion of a polymer having organic acid functional groups and a polyfunctional crosslinking agent having functional groups capable of reacting with organic acid groups, as described in U.S. Pat. No. 5,702,754, the disclosure of which is incorporated herein by reference.

The release rate of drugs from drug matrix layers is largely controlled, for example, by variations in the polymer structure and formulation, the diffusion rate of decomposition or dissolution of the polymer coefficient of the matrix, the solvent composition, the ratio of drug to polymer, potential chemical reactions and interactions between drug and polymer, the thickness of the drug adhesion layers and any barrier layers, and the process parameters, e.g., drying, etc. The coating(s) applied by the methods and apparatuses of the present invention may allow for a controlled release rate of a coating substance with the controlled release rate including both long-term or a burst release where all of the drug is released at a predetermined time.

Additionally, a coating substance may include suspension particles, e.g., a powder. The suspension particles are not utilized for suspending the medical devices, but rather, are coated onto the medical devices. For example, the suspension particles may be fused to the surface of the medical device by a coating solution, or melting a coating onto the device.

The coatings of the present invention are applied such that they result in a suitable thickness, depending on the coating material and the purpose for which the coating(s) is applied. As an example, coatings applied for localized drug delivery are typically applied to a thickness of about 1 to 30 microns, preferably about 2 to 20 microns. Very thin coatings, e.g., of about 100 Å, and much thicker coatings, e.g., more than 30 microns, are also possible. It is also within the scope of the present invention to apply multiple layers of the same or different coating materials, which may perform identical or different functions (e.g., to provide for biocompatibility, to control drug release, etc.).

In accordance with a first embodiment of the present invention, medical devices are coated by suspending the medical device in an air stream substantially devoid of suspending particles having a first coating material dispersed therein, by any corresponding, suitable method. For illustrative purposes only, the first embodiment of the invention is described with specific reference to the so-called "Wurster process" shown in FIG. 1. The Wurster process is described in U.S. Pat. No. 3,253,944, which is incorporated herein by reference. Such a process has been proposed for use to coat pharmaceutical tablets with waxes (see, e.g., D. M. Jones, "Factors to Consider in Fluid-Bed Processing," 9 *Pharm. Tech.* 50-62 (1985), and A. M. Mehta, "Scale-Up Considerations in the Fluid-Bed Process for Controlled-Release Products," 12 *Pharm. Tech.* (1988)), but has not been proposed or used to coat medical devices.

As stated above, the first embodiment for an apparatus for coating medical devices 100 in accordance with the principles of the present invention is illustrated in FIG. 1. In FIG. 1, medical devices 110 are placed in a chamber 120. The chamber 120 includes a top opening 121 for exhaust, a bottom opening 122 for introduction of input air 140, and at least one side wall 123. Although the chamber 120 is shown to generally include a structure having a tapered, cylindrical shape, the chamber 120 may be of any suitable shape, such as rectangular. The tapered configuration of the chamber 120 as shown in FIG. 1 is generally preferred to facilitate a cyclical air flow within the chamber 120. The coating process of the present invention occurs within the chamber 120.

The embodiment 100 includes an air distribution plate 130, which is secured to the side wall 123 of the chamber 120. The air distribution plate 130 has openings 131 that are smaller than the smallest dimension of the medical devices 110 so that the medical devices 110 cannot fall through it. The purpose of the air distribution plate 130 is to channel input air 140, introduced into the chamber 120 from its bottom opening 122, into the coating region 150 of the chamber 120 to assist in the fluidization and coating of the medical devices 110. The air distribution plate 130 is of any suitable shape to achieve this purpose, such as planar (as shown in FIG. 1) or concave configurations.

The air distribution plate 130 is of any suitable structure that permits the flow of air therethrough such as, for example, a perforated metal or ceramic plate or screen. Preferably, the air distribution plate 130 has an open area (i.e., the planar surface area of openings) of about 4 to about 30 percent, such as about 4, 6, 8, 12, 16 or 30 percent. A specific example of the air distribution plate 130 is a stainless steel screen having an opening size of about 60 to about 325 mesh. The open area and opening size of the air distribution plate 130 are selected to provide for the optimum suspension and coating of the medical devices 110 within the coating region 150. For example, an air distribution plate 130 having a large open area will result in a relatively low velocity of air within the coating region 150, and is thus used for low density medical devices 110. Conversely, an air distribution plate 130 having a small open area will result in a relatively high velocity of air within the coating region 150, and is thus used for high density medical devices 110. The air distribution plate can be either fixed or rotating to facilitate more even distribution of air.

The embodiment 100 further includes a nozzle 160 extending through the air distribution plate 130 and into the coating region 150. The nozzle injects an air stream 161, which in this embodiment includes a coating material dispersed therein, into the coating region 150. As shown in FIG. 1, the nozzle 160 is preferably located at or near the longitudinal axis of the chamber 120. The embodiment 100 optionally includes multiple nozzles situated at various locations within the chamber 120, such as along the side 123, top, or bottom of the chamber 120. In this embodiment, the nozzle 160 is used to introduce one or more coating materials, sequentially or simultaneously, into the chamber 120. Where multiple coating materials are introduced into chamber 120, they may be either mixed and introduced at nozzle 160, i.e., in-line mixed, or may be introduced into chamber 120 though nozzle 160 and/or from the nozzles located at the top or bottom of the chamber.

Both air streams 161 and 140 are substantially devoid of suspending particles, as discussed above, and the air streams may consist of one or more gases. Because the air streams are substantially devoid of any suspending particles, the surface areas of the medical devices to be coated when in the air stream(s) are not subject to being obscured by, and/or damaged by contact with, the suspending particles, which could deleteriously impact the coating of the surface areas of the medical devices. In an embodiment, air stream 161 is characterized by a higher velocity than air stream 140 that is channeled through the air distribution plate 130 to cause a cyclical air flow and corresponding medical device movement within the coating region 150. In other words, the high-velocity air stream 161 causes the medical devices 110 to be lifted from or near the air distribution plate 130 towards the top opening 121 of the chamber 120. When the air stream 161 can no longer support the medical devices 110, they fall through the lower-velocity air stream 140 along the sides of the chamber 120. The velocity of the air stream 140 is sufficient to slow, but not to stop or reverse, the fall of the medical devices 110. When the medical devices 110 approach or fall on the air distribution plate 130, they are again lifted by the high-velocity air flow 161. Thus, air streams 161 and 140 are of a sufficient velocity such that the air streams themselves are able to suspend the medical devices within the coating region. Thus, no suspending particles are required in the air streams to suspend the medical devices to be coated.

In an embodiment where multiple nozzles are used, nozzle 160, centrally located near the air distribution plate 130 as shown in FIG. 1, may be the only nozzle associated with a high-velocity air stream. Any other nozzles may be only used to inject the coating material(s) into the chamber 120 at a low velocity so as not to disrupt the cyclical flow of air and medical devices.

An optional partition 170, which is preferably tubular in shape, may be attached to the side wall 123 of the chamber 120 and extend along the longitudinal axis of the chamber 120 to help facilitate the cyclical air flow within the chamber 120 and to ensure the separation of rising and falling medical devices 110, thus minimizing potentially damaging interactions. Also optional is a gas exhaust duct 180, which is preferably associated with top opening 121 and which may include a filter.

In an alternative embodiment, the air streams 161 and 140 may be of substantially equal velocity. In this embodiment, the flow/velocity of the two air streams at the center of the chamber 120 would be additive to effectively create a greater flow/velocity of air at the center of the chamber in comparison to the flow/velocity of the air at the sides of the chamber, thus providing for cyclical movement of the medical devices as described above.

In yet another alternative embodiment, only one of air streams 161 or 140 are utilized. For example, the airstream 161 is utilized to both suspend the medical devices and introduce the coating material(s) into chamber 120. A cyclical flow of air within the chamber could be provided by varying the velocity of the one air stream across its flow pattern, such as, for example, by appropriately configuring the openings in air distribution plate 130.

Although the embodiment 100 making use of the Wurster process is generally preferred for making the coated medical devices of the present invention, any suitable method or apparatus can be used. For example, medical devices may be loaded into a conventional fluidized bed chamber, in which air is introduced into a "bed" or layer of the medical devices from below while the coating material is sprayed onto the fluidized devices from above. In such a process, the medical devices will move randomly within a fluidized bed. Airless and atomized air spray processes are also within the scope of the present invention. Although not required by the present invention, coating within a closed chamber is generally preferred because of the corresponding ability to control the coating processing parameters and the chamber environment. For example, it is advantageous to control processing parameters such as the fluidization air composition, temperature and humidity when coating with drugs or polymers that degrade, oxidize, hydrolyze, etc., upon exposure to specific environments. The present invention may be utilized to coat medical devices with organic-based coating materials. Thus, operating temperatures in at least some embodiments of the apparatuses and methods of the present invention are generally less than 500° C., with some embodiments having an operating temperature of between 0° C.-200° C. The particular operating temperatures utilized are compatible with the particular coating materials. Thus, operating temperatures compatible with all of the coatings materials disclosed herein can be established and maintained in the apparatuses and methods of the present invention.

In other alternative embodiments of the present invention, instead of applying a coating as a preformed substance, the material of the coating would be generated in the spraying process. The suspended medical devices to be coated could be sprayed first with a polyfunctional condensation monomer followed by spraying with a complementary condensation polyfunctional monomer to provide a polymer coating by interfacial polymerization. For example, a glycol or diamine could be sprayed on first followed by a diisocyanate to form a polyurethane or polyurea. A potential advantage of this process would be to avoid the need for volatile solvents, application of lower viscosity fluids to improve coverage, and to provide crosslinked polymer coating that would be impossible to obtain by conventional coating techniques, e.g., by use of trifunctional monomers.

Other alternative embodiments for coating of the medical devices include apparatuses and methods that do not involve dispensing the coating material using an air stream through, for example, nozzle 160 as discussed above in connection with FIG. 1. These alternative apparatuses and methods for coating the medical devices still utilize an air stream and the structure of FIG. 1, as described above, to suspend the medical devices in a coating chamber; however, the medical devices could be coated by using alternative coating techniques. These alternative coating techniques could also be utilized with the fluidized bed chamber contemplated above.

Figure 2:
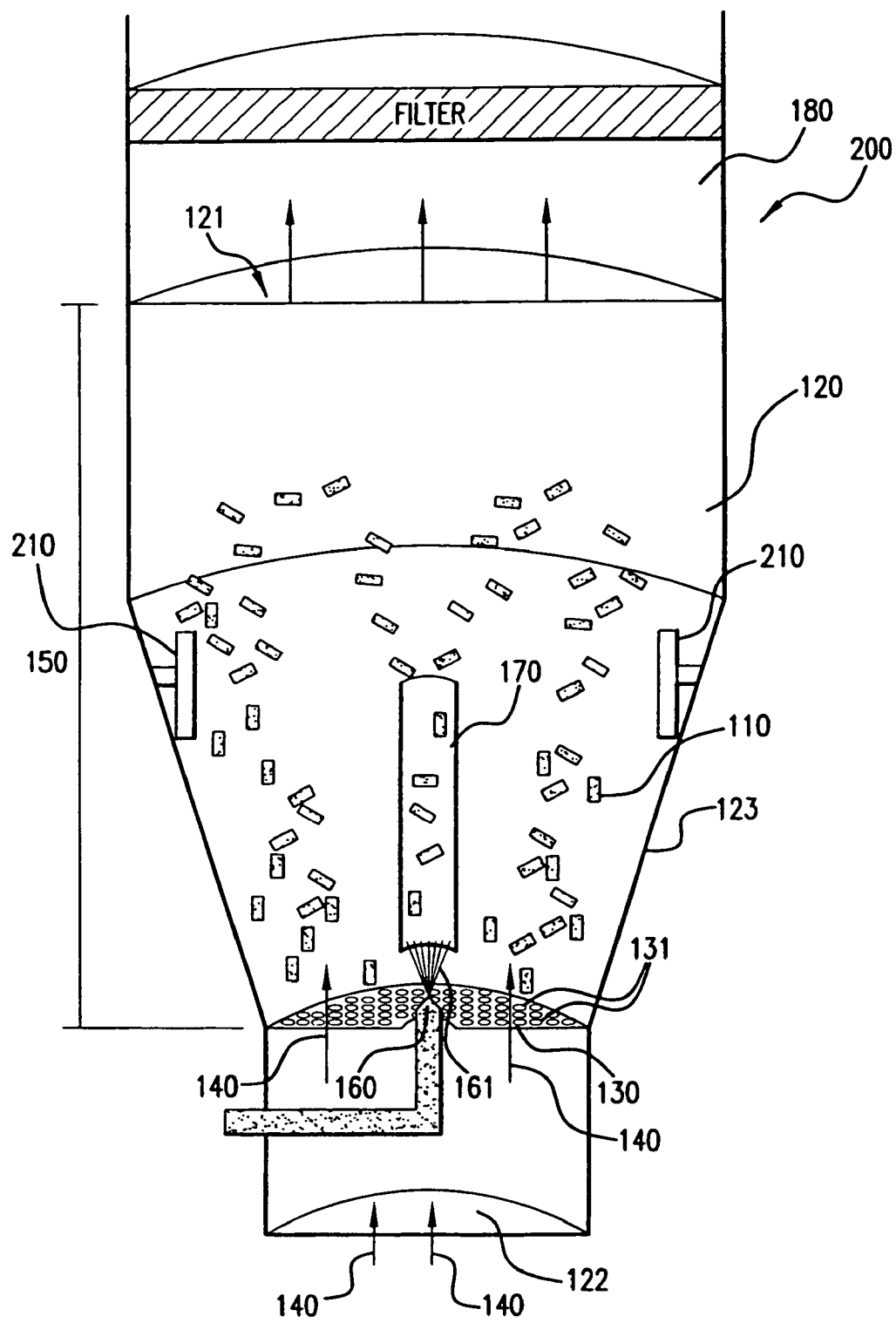
FIG. 2 is a cross-sectional view of an apparatus for coating medical devices in accordance with a second embodiment of the present invention.

Thus, a second embodiment for an apparatus for coating medical devices 200 in accordance with the principles of the present invention is illustrated in FIG. 2. The embodiment of FIG. 2 utilizes a structure similar to that described for the embodiment of FIG. 1, however, in the embodiment of FIG. 2, the coating material may not be dispersed within air stream 161 by nozzle 160. In the embodiment of FIG. 2, both or one of the air streams 161 and 140 are utilized to suspend the medical devices within chamber 120. A coating apparatus 210 is utilized to apply the coating to the suspended medical devices. Depending upon the particular coating apparatus used, a coating material may be introduced into the coating chamber by the coating apparatus itself, by one or both of air streams 161 and 140, or through any other well-known means that are associated with the particular coating apparatus utilized. For reference purposes, the components for embodiment 200 in FIG. 2 that are common to those of embodiment 100 of FIG. 1 are designated by like reference numerals.

In the embodiment of FIG. 2, the coating apparatus 210 may include a device(s) that permit the use of any number of alternative techniques for coating the medical devices. As discussed previously, the coating apparatus may apply a single coating or multiple coatings to the medical device. Additionally, the coating apparatus may apply coatings to any of the different types of medical devices disclosed previously in this specification. The apparatus may also apply any of a variety of coating materials as described previously.

The coating apparatus 210 may be utilized to apply one or more coatings to medical devices by utilizing any of the following exemplary techniques and the associated devices for these techniques for application of the coatings.

Ionization deposition processes can be utilized to apply coatings to medical devices. Ionization deposition processes such as ion beam-assisted deposition (IBAD), ion beam (IB), and ion beam implantation (IBI). Examples of materials that can be deposited/implanted include nitrogen, gold, silver, tungsten, titanium, aluminum, silicon, iron, nickel, selenium, tantalum, diamond-like carbon (DLC), ceramics, radioactive materials such as palladium-103, $^{60}$Co, $^{192}$Ir, $^{32}$P, $^{111}$In, $^{90}$Y, and $^{99}$Tc.

Plasma treatment, grafting, or deposition processes can be used to coat or modify the surface of the medical device or a part of the medical device with the following materials: monomers or oligomers, cyclic and acrylic siloxanes, silanes, silylimidazoles, fluorine-based monomers (hydrofluorocarbons), aliphatic and aromatic hydrocarbons, acrylic monomers, N-vinyl pyrrolidone, vinyl acetate, ethylene oxide, one or more monomers used alone or in combination in order to form blends, cross-linked polymers, copolymers and interpenetrating network polymers. Plasma treatment may also be used to enhance crosslinking and/or improve surface properties such as adhesion, lubricity, or conductivity.

Figure 3:
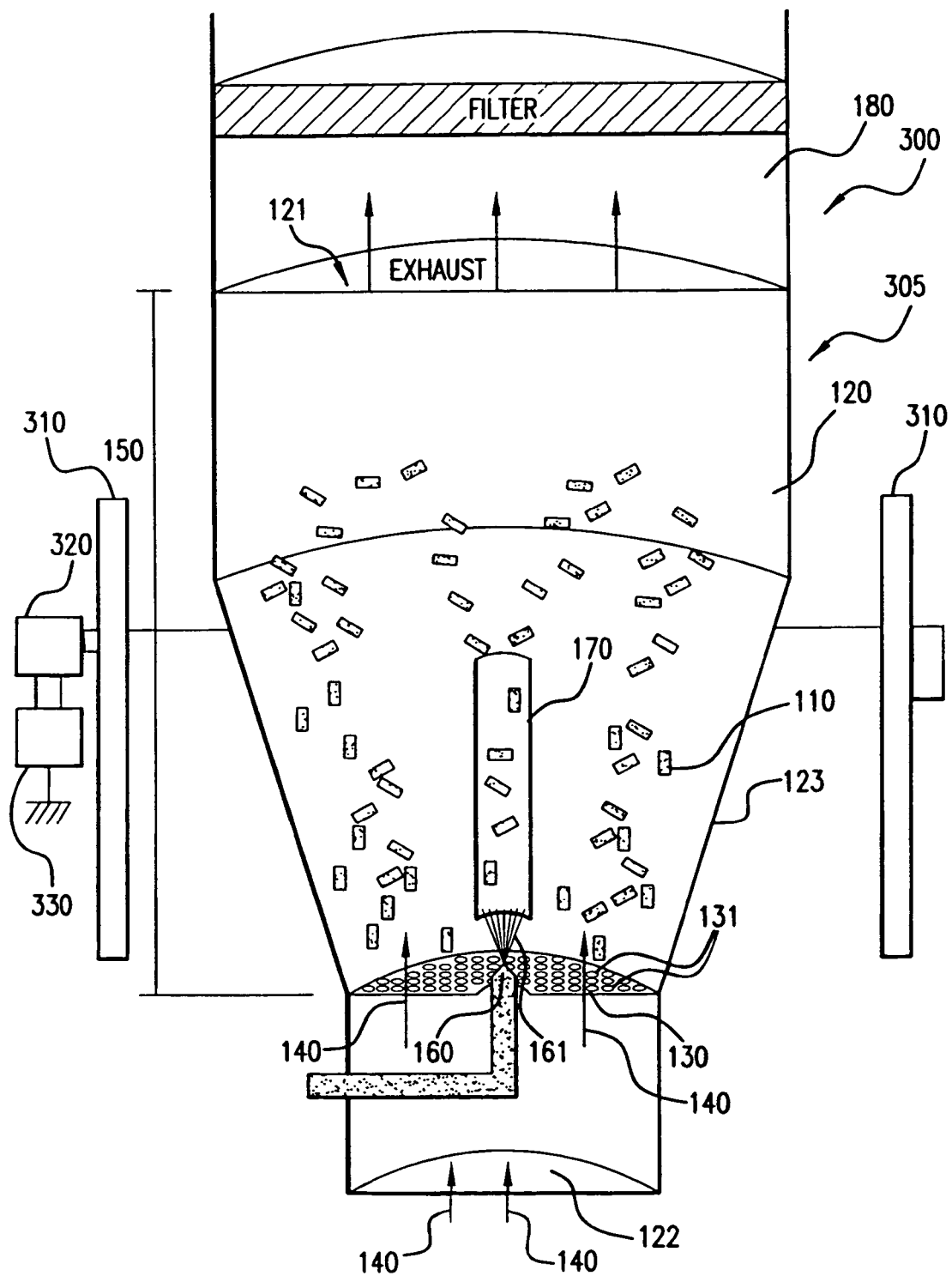
FIG. 3 illustrates a plasma coating apparatus in accordance with the principles of the present invention.

FIG. 3 illustrates a particular alternative embodiment for an apparatus for coating medical devices 300 in accordance with the principles of the present invention where the coating apparatus 210 of FIG. 2 is a plasma coater 305. As described in connection with FIG. 2, in the embodiment of FIG. 3, both or one of the air streams 161 and 140 are utilized to suspend the medical devices within chamber 120; however, a plasma coater 305 is utilized to coat the suspended medical devices. For reference purposes, the components for embodiment 300 in FIG. 3 that are common to those of embodiments 100 and 200 of FIGS. 1 and 2, respectively, are designated by like reference numerals. Plasma coater 305 includes electrodes 310, a matching network 320, and a RF (radio frequency) generator 330. The materials to be coated on the medical devices may be introduced into chamber 120 through either of air streams 161 and/or 140 or through any other means, such as by depositing the coating material on air distribution plate 130 and having the air stream(s) dispense the coating material into the chamber. The coating material(s) are then applied to the medical devices by using plasma coater 305.

In continuing with the discussion of the alternative coating techniques that may be utilized in the present invention, chemical vapor deposition processes are also within the scope of the present invention, employing polymers such as polyamide, polyimide, parylene, and parylene derivatives, polyalkylene oxide, polyalkylene glycol, polypropylene oxide, silicone based polymers, polymers of methane, tetrafluoroethylene or tetramethyldisiloxane or polymers from photopolymerizable monomers or combinations thereof.

Deposition may be utilized in the present invention as well as, polymerization or treatment of part of the medical device surface or the entire device surface using microwave, ultraviolet light (UV), visible light, e-beam, and thermal evaporation techniques.

In any embodiment of the present invention, the apparatuses and methods of the present invention result in the complete or partial coating of the medical device to be coated. Partial coating is accomplished, for example, using known masking or similar techniques to result in the coating of predetermined struts or stent segments. The various coating techniques may be used in conjunction with one another and, thus, they are not mutually exclusive.

In addition to the previously described coating layers and their purposes, in the present invention the coating layer or layers may be applied for any of the following additional purposes or combination of the following purposes:

Alter surface properties such as lubricity, contact angle, hardness, or barrier properties.

Improve corrosion, humidity and/or moisture resistance.

Improve fatigue, mechanical shock, vibration, and thermal cycling.

Change/control composition at surface and/or produce compositionally graded coatings.

Apply controlled crystalline coatings.

Apply conformal pinhole free coatings.

Minimize contamination.

Change radiopacity.

Impact bio-interactions such as tissue/blood/fluid/cell compatibility, antiorganism interactions (fungus, microbial, parasitic microorganisms), immune response (masking).

Control release of incorporated therapeutic agents (agents in the base material, subsequent layers or agents applied using the above techniques or combinations thereof).

Or combinations of the above using single or multiple layers.

In addition to the benefits of the apparatus and methods of the present invention that have been discussed previously in this specification and in further amplification of some of the benefits discussed previously, the present invention can provide the following advantages.

Coating in an air stream allows many medical devices or parts of medical devices to be coated simultaneously in batch process, which eliminates variability that could arise if each object is coated and handled individually.

Part to part variability is minimized because all the objects are coated under identical conditions at the same time.

Uniformity of the coated layer, layers, or surface modification is achieved over the entire surface of interest using careful control and optimization of the coating parameters.

In situations where the device, part of the device and/or any subsequently coated layers contain one or more therapeutic agents, the methods yield a uniform, well-defined rate controlling membrane, or a uniformly coated layer incorporating the therapeutic agents. This results in uniform controlled drug release for devices, parts of devices, and/or coatings that contain active components.

Drug reconciliation and traceability (a critical issue in finished pharmaceutical manufacturing processes) is maximized using this type of contained manufacturing process in situations where the device, part of the device, and/or any subsequently coated layers contain one or more therapeutic agents.

No defects will form on the surface as a result of holding the device during coating since the coating is applied to the device while the device is levitated in the air stream.

Worker exposure to harmful chemicals, or components is minimized because the process proceeds under sealed conditions.

One coater may be used to apply more than one type of coating and/or surface modification if the equipment is designed to handle combinations of several coating techniques such as air atomization, ionization deposition, plasma, chemical vapor deposition, UV, microwave, visible, and e-beam.

Figure 4:
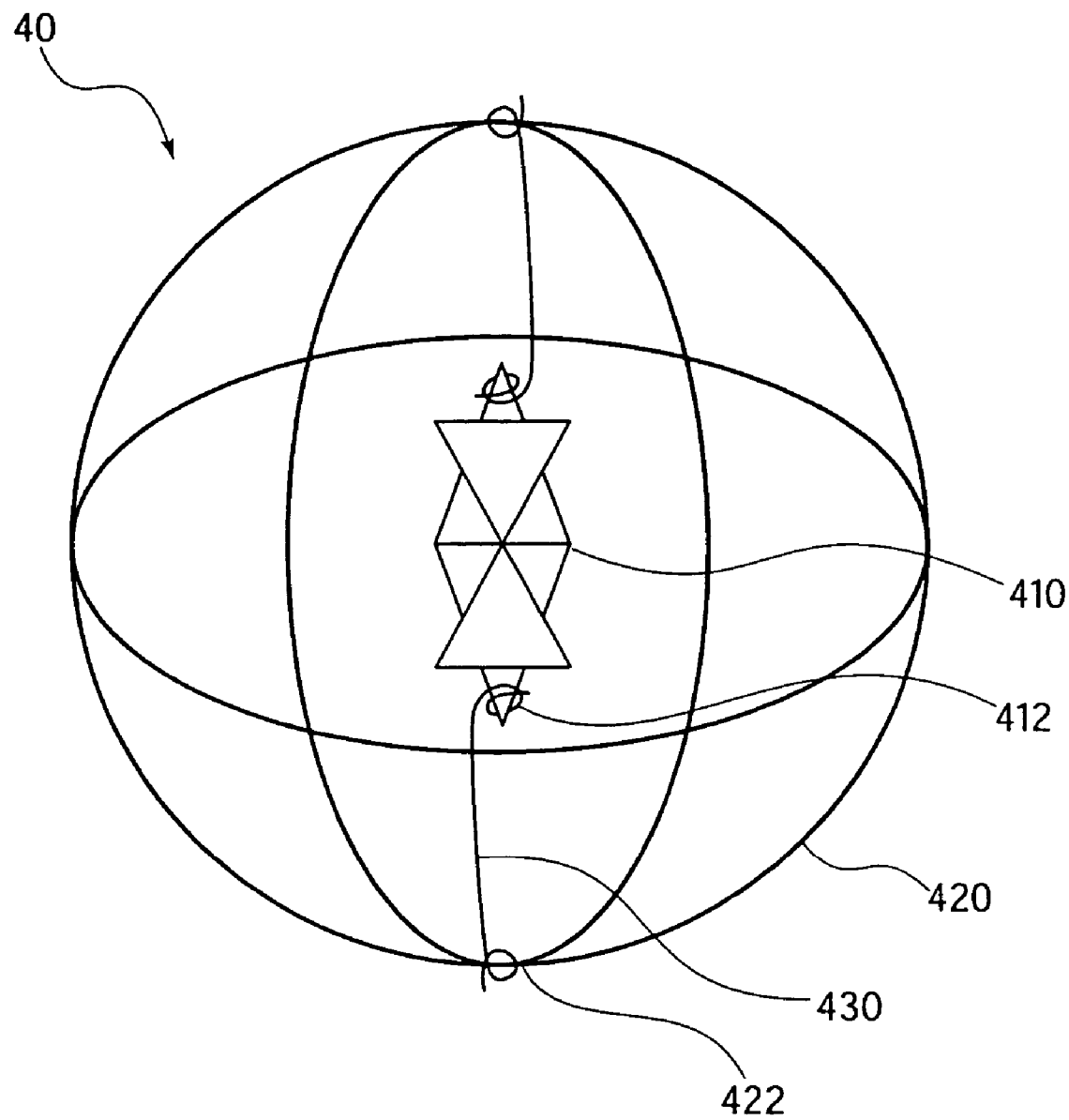
FIG. 4 is a perspective view of a protective device in accordance with a third embodiment of the present invention.

FIG. 4 is a perspective view of an exemplary embodiment of a protective device 40 of the present invention, which can be used to protect at least one medical device from abrasion, scratches, etc. before, during, and/or after a coating process.

Figure 5:
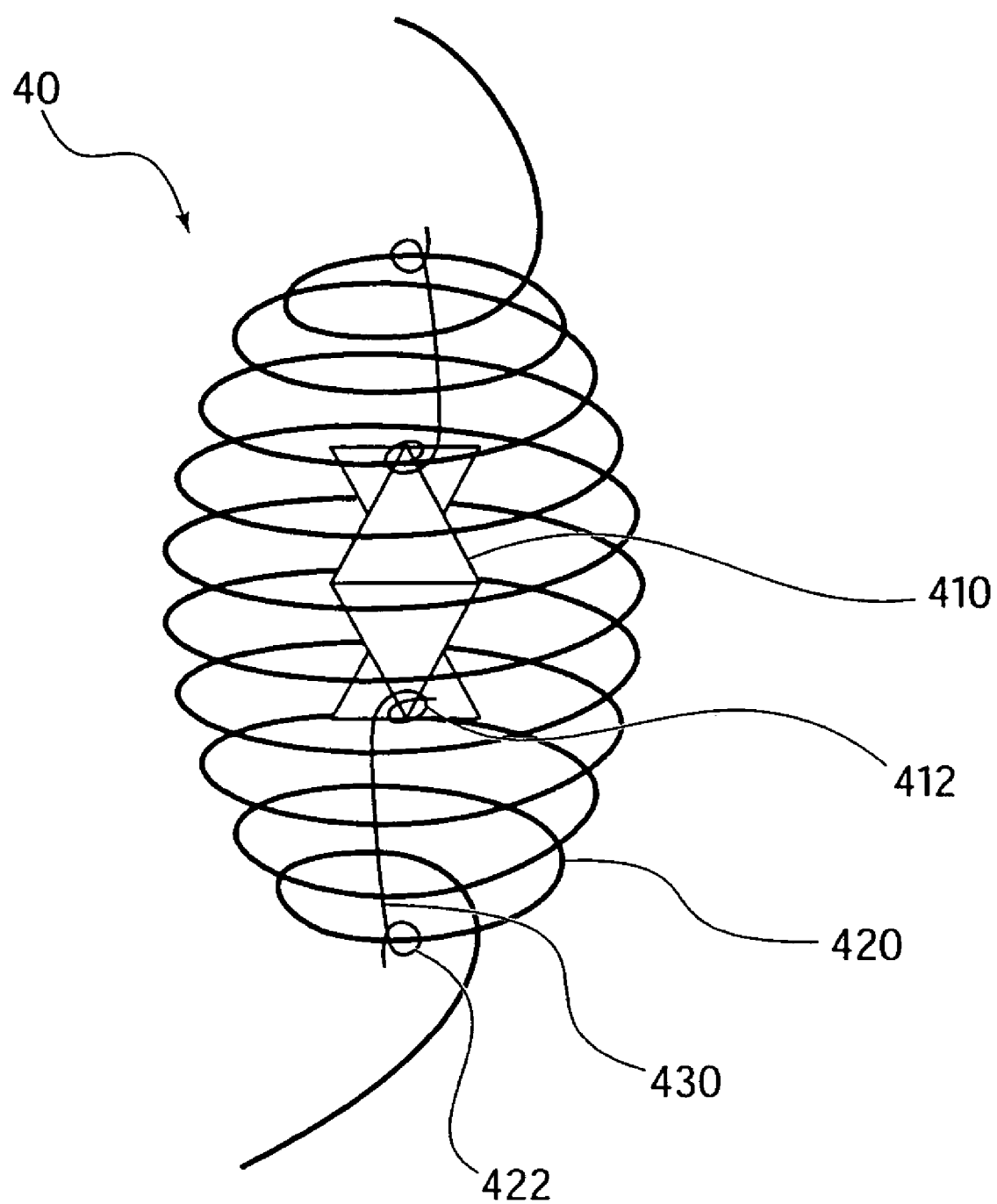
FIG. 5 is a perspective view of a protective device in accordance with another embodiment of the present invention.

FIG. 5 is a perspective views of another exemplary embodiment of a protective device 40 of the present invention.

Referring to FIGS. 4 and 5, medical device 410 can be non-contactably surrounded by a open-structure cage 420. In one embodiment, such as that shown in FIG. 4, the structure of cage 420 can resemble a plurality of solid and/or hollow circular and/or elliptical rings that are distributed about a common central point and connected to each other at their intersections. Thus, cage 420 can be described as including a ring wall that defines an open structure.

In another embodiment, such as that shown in FIG. 5, the structure of cage 420 can resemble a helical spring having a longitudinal axis and having a diameter that can bulge near the longitudinal middle of the helix and can reduce near its longitudinal ends. Thus, cage 420 can be described as including a helical wall that defines an open structure.

One or more securements 430 can contact (e.g., be integral to, be attached to, bear upon, etc.) cage 420 at one or more cage contact points 422, and can contact medical device 410 at device contact points 412. Securements 430 can take various forms, including strings, strands, wires, bands, arms, and the like. For example, as shown in FIG. 4, securements 430 can be wires that are tied to medical device 410 and to cage 420. As another example, and as shown in FIG. 5, securements 430 can be rubber bands that bear upon medical device 410 and cage 420.

Cage 420 and/or securements 430 can be constructed of a solvent-resistant material, such as a metal and/or an inert polymer. For example, cage 420 and/or securements 430 can be constructed of stainless steel, niconel, and/or teflon. As another example, cage 420 and/or securements 430 can be constructed of any appropriate base material, and coated with a solvent-resistant and/or solvent-inert material.

In application, medical device 410 can be introduced into cage 420 without directly contacting cage 420. As described above, one or more of securements 430 can contact cage 420. There are numerous feasible manners in which securements 430 can contact cage 420. For example, as shown in FIG. 4, any of securements 430 can be attached to (looped, tied, stapled, welded, and/or brazed, etc.) cage 420 at any of several cage contact points 422.

In addition, one or more of securements 430 can contact medical device 410. There are numerous feasible manners in which securements 430 can contact medical device 410. For example, as shown in FIG. 4, any of securements 430 can be attached to (looped, tied, etc.) medical device 410 at any of several device contact points 412.

As another example, and as shown in FIG. 5, any of securements 430 can bear against cage 420 at any of several cage contact points 422, and can bear against medical device 410 at any of several device contact points 412. In any event, cage 420 can combine with securements 430 to constrain the movement of medical device 410 within cage 420, thereby protecting, securing, and/or stabilizing medical device 410.

Once medical device 410 is secured within cage 420, the combination can be suspended in an air stream that is substantially devoid of suspending particles. A first coating material can be introduced into the air stream, such that at least a portion of a first surface of the suspended medical device is coated. Before, during, and/or after the coating process, the combination of cage 420 and securements 430 can protect medical device 410 from contact with other medical devices 410, the coating chamber (not shown), and/or other structures that can scratch and/or damage medical device 410. When the coating process is complete, including any needed drying, curing, etc., medical device 410 can be removed from cage 420 and packaged for inventory and/or shipment to a medical service provider.

Because the open structure of cage 420 can be relatively lightweight, the combination of medical device 410, cage 420, and securements 430 can similarly be relatively lightweight. Such a combination of medical device 410, cage 420, and securements 430 can be lifted, levitated, and/or suspended by the air flow present in the coating chamber similarly to that described earlier for the medical device alone. Thus, the use of this combination can enable the coating of the medical device while effectively eliminating the likelihood of damage to that device and/or its coating from physical contact with other medical devices, the coating chamber, the distribution plate, and/or nozzles, etc.

FIGS. 6 through 9 show additional embodiments of the present invention. In these figures various coating devices that employ vibration to move medical devices during their coating are illustrated. A common element shared by each of these devices is a vibrating structure above which medical devices can be coated.

Figure 6:
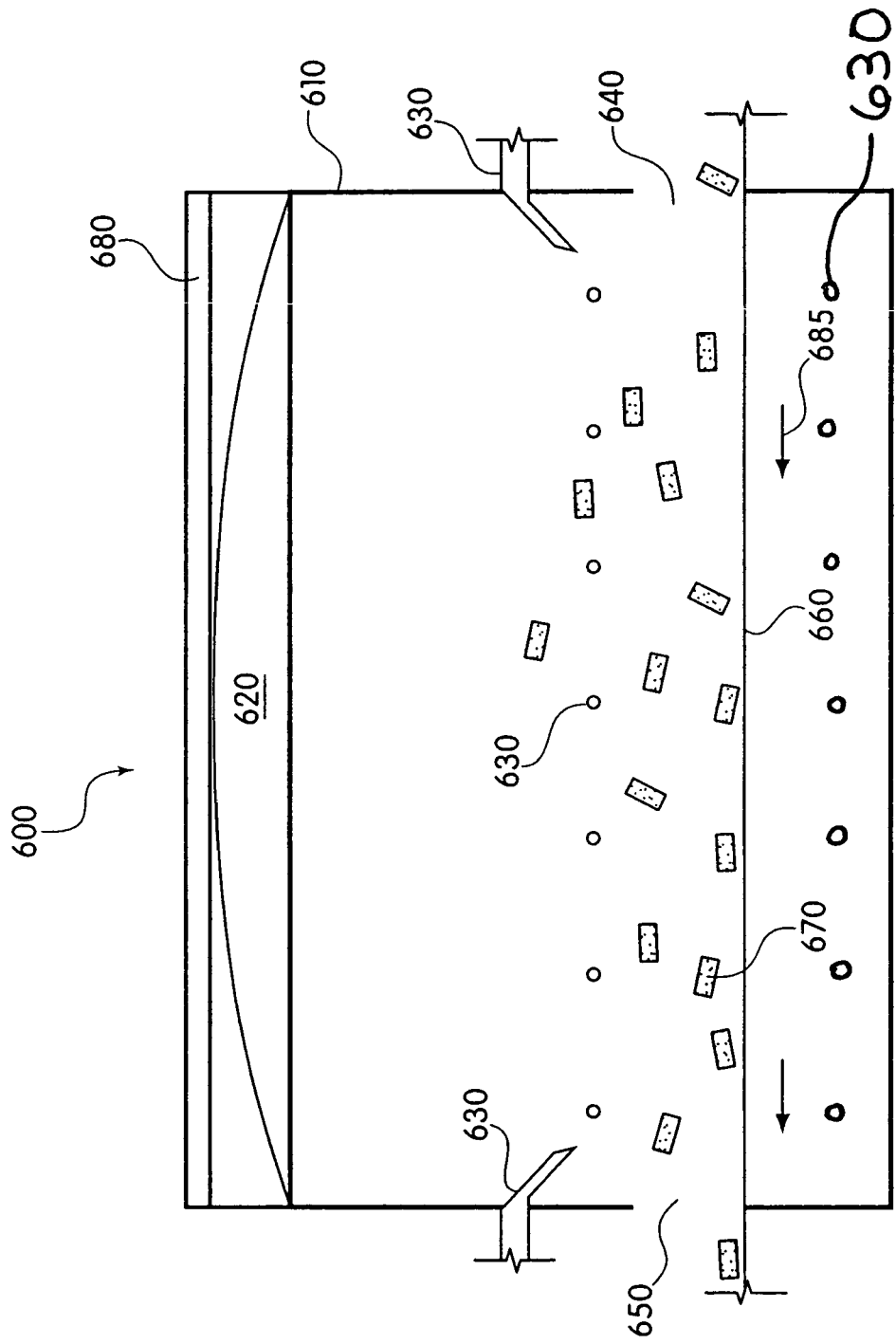
FIG. 6 illustrates a conveyor belt coating apparatus in accordance with another embodiment of the present invention.

FIG. 6 shows a coating device 600 that may be employed in accord with an alternative embodiment of the present invention. This coating device 600 may be used to coat the medical devices 670 that may be located within coating chamber 610. Visible in FIG. 6 are exhaust filter 680, exhaust 620, spray nozzles 630, medical devices 670, conveyor belt 660, entrance opening 640, and exit opening 650.

In FIG. 6, the conveyor belt 660 (which is the vibrating structure in this embodiment) is shown positioned within a coating chamber 610. This belt 660 is capable of moving medical devices 670 placed thereon from the entrance 640 to the exit 650. As can be seen in FIG. 6 the medical devices 670 in the coating chamber 610 are located both on and above the conveyor belt 660. These medical devices 670 are bounced above the conveyor belt 660 as a result of the vibration of the conveyor belt 660. Thus, in use, as the conveyor belt 660 moves the medical devices 670 in the direction of the arrow 685, its may also, through its vibration, cause the medical devices to jump in the air.

As the medical devices are moved and bounced through the coating chamber 610 a coating may be released by nozzles 630 into the coating chamber 610. As this coating comes in contact with the medical devices, due to the random nature of their movement, the entire surface of each of the medical devices 670 may become coated with the coating material.

During this coating process, extraneous coating may be exhausted by exhaust 620, through filter 680, into a recycling chamber (which is not shown) or, alternatively, directly into the surrounding air. In either case, the extraneous coating may be expelled between coating cycles or continuously removed during the coating process.

A second coating may also be introduced into the coating chamber 610 during the coating process. This second coating may be introduced after the first coating has been expelled from the coating chamber, concurrent with the introduction of the first coating and shortly after the application of the first coating. To assist in curing or drying either the first or the second coating, heat or some other curing catalyst may be introduced into the coating chamber 670. The curing catalyst employed may be determined based upon the coating being used, the medical device being coated or some other factor.

In this embodiment, the physical contact of the medical devices 670 with the vibrating conveyor belt 660 forces the medical devices to become suspended or bounce above the conveyor belt 660 in the coating chamber 610 during the coating process. In other embodiments, this type of physical impact may be replaced or supplemented by pressure wavefronts that are created by the vibration of the structure. These wavefronts, which may be acoustic, can be generated at a predetermined frequency or simply at random.

While eight coating sources or nozzles 630 are shown in FIG. 6, any number of coating nozzles 630 can be used to coat the medical devices 670. Additionally, while each of the nozzles 630 are shown at the same elevation up the side of the coating chamber 610 they may, instead, be located at different elevations and also at different spacings dependant upon the individual circumstances. They may also be located in other positions as well including the top and bottom of the coating chamber. It is preferable, however, that whatever spacings and locations are chosen, the nozzles are located and oriented in a position that can direct coating to the medical devices that are above and on the vibrating structure.

As noted above, these coating nozzles can eject a single coating material during the entire coating process or multiple coating materials, each being ejected or delivered at different times or simultaneously, as required, during the coating process. When multiple coatings are being applied, they may be delivered or sprayed to form composite layers, individual layers and any other desired coating configuration. Furthermore, the coating nozzles 630 can each concurrently spray different coating materials so that each medical device 670 can be coated with a different coating dependent upon its location within the coating chamber 610 when the coatings are being delivered. In this configuration the spacing between devices may be increased to reduce the risk of over spray and to control the distribution of coating onto each device.

As discussed above, any coating not adhered during this process or any other process may be exhausted out of the coating chamber 610 through exhaust 620. While the exhaust is shown near the top of the chamber 610 it may be placed at other locations as well, including below the vibrating conveyor belt 660. Coating that is recovered may be stored and reused at a later time. Moreover, while a passive exhaust is employed in this embodiment an active one that uses pressure (positive or negative) to force coating into the exhaust may also be employed.

In another embodiment of the present invention, rather than moving through a single coating chamber the conveyor belt may move through more than one. Each of these chambers may contain a different coating or a different coating environment (i.e. a different temperature, ambient pressure; etc.). Moreover, rather than having the single conveyor belt as shown in FIG. 6, two or more belts may be used in alternative embodiments.

Figure 7:
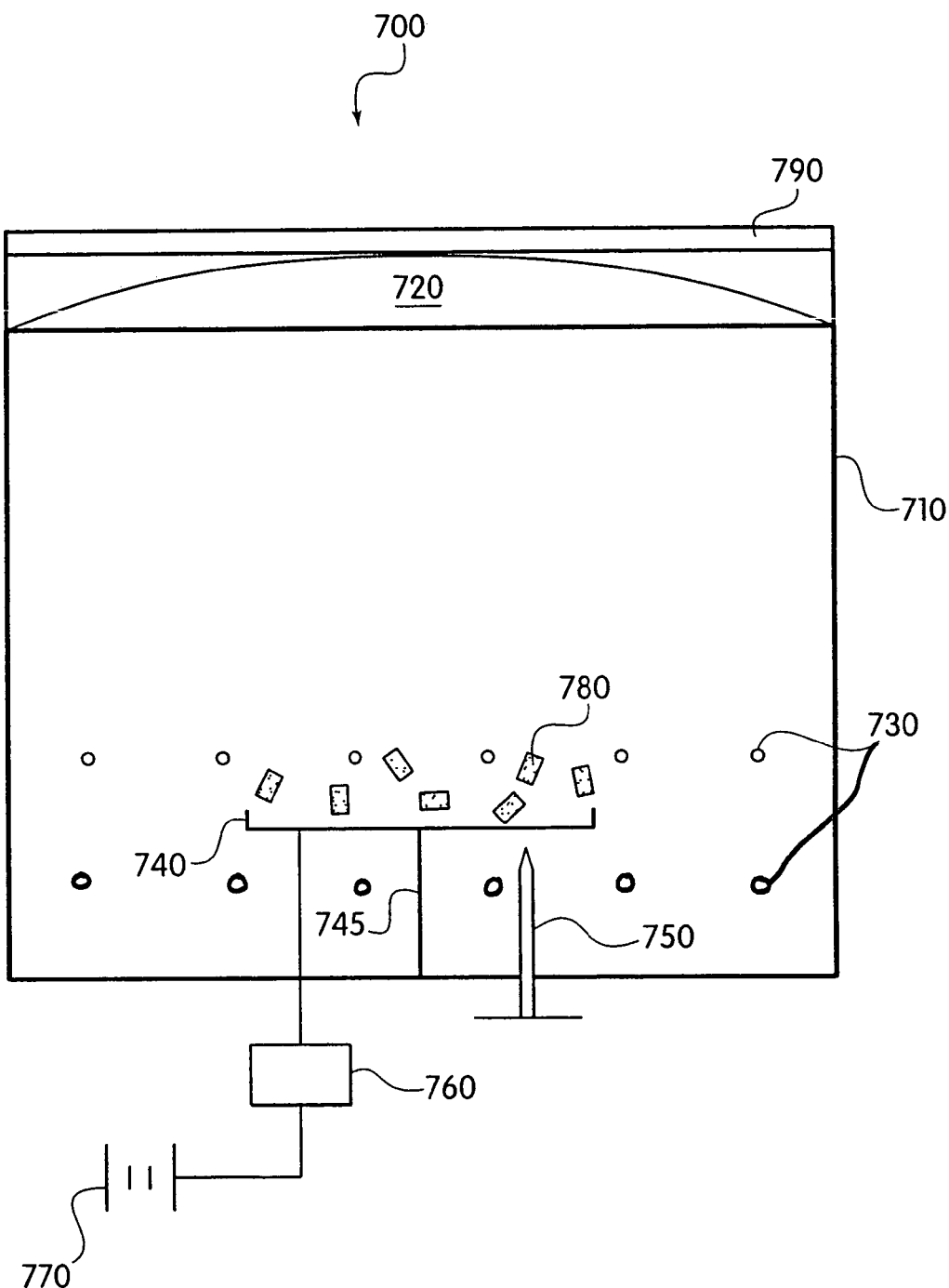
FIG. 7 illustrates a vibrating plate coating apparatus in accordance with another embodiment of the present invention.

FIG. 7 shows another alternative embodiment of the present invention. In FIG. 7 a coating device 700 that may coat one or more medical devices 780 is shown. In this embodiment, the medical devices 780 are placed on a rigid vibrating structure or plate 740 which may be made from steel, aluminum, and numerous other metals or rigid materials. The vibrating plate 740 in this embodiment may be attached to a frequency generator 760, which is itself coupled to and driven by a power source 770.

Also visible in FIG. 7 are the coating sources 730, support 745, and nozzle 750. During use, the vibrating plate 740 may be vibrated by the frequency generator while a compressed gas is ejected by the nozzle 750. Each of these may generate forces that are sufficient to move medical devices 780 off of the vibrating structure 740. In combination, however, they may move and lift these devices even further than either could individually. The frequency generator 760 may act to vibrate the vibrating structure 740 at a single frequency or at multiple frequencies, changing over time, depending upon the height that the medical devices 780 need to be moved as they are coated.

As the medical devices 780 are suspended, and in accord with the above embodiment, the medical devices can be coated with a coating material sprayed into the coating chamber 710 through coating nozzles 730. Single and multiple coating layers can be achieved with a single coating material and with different coating materials layered upon each other. When multiple coating layers are desired the coating may be injected into the chamber at various intervals to allow for drying or curing to occur. During each of these intervals, the excess coating material can be exhausted through the exhaust 720. Here again, the location of the coating nozzles 730 and the exhaust 720 are not intended to be limiting.

When the nozzle 750 is employed it is preferred that the gas stream ejected from it be substantially devoid of suspending particles. In so doing potential damage to the coating on the medical device can be minimized.

Figure 8:
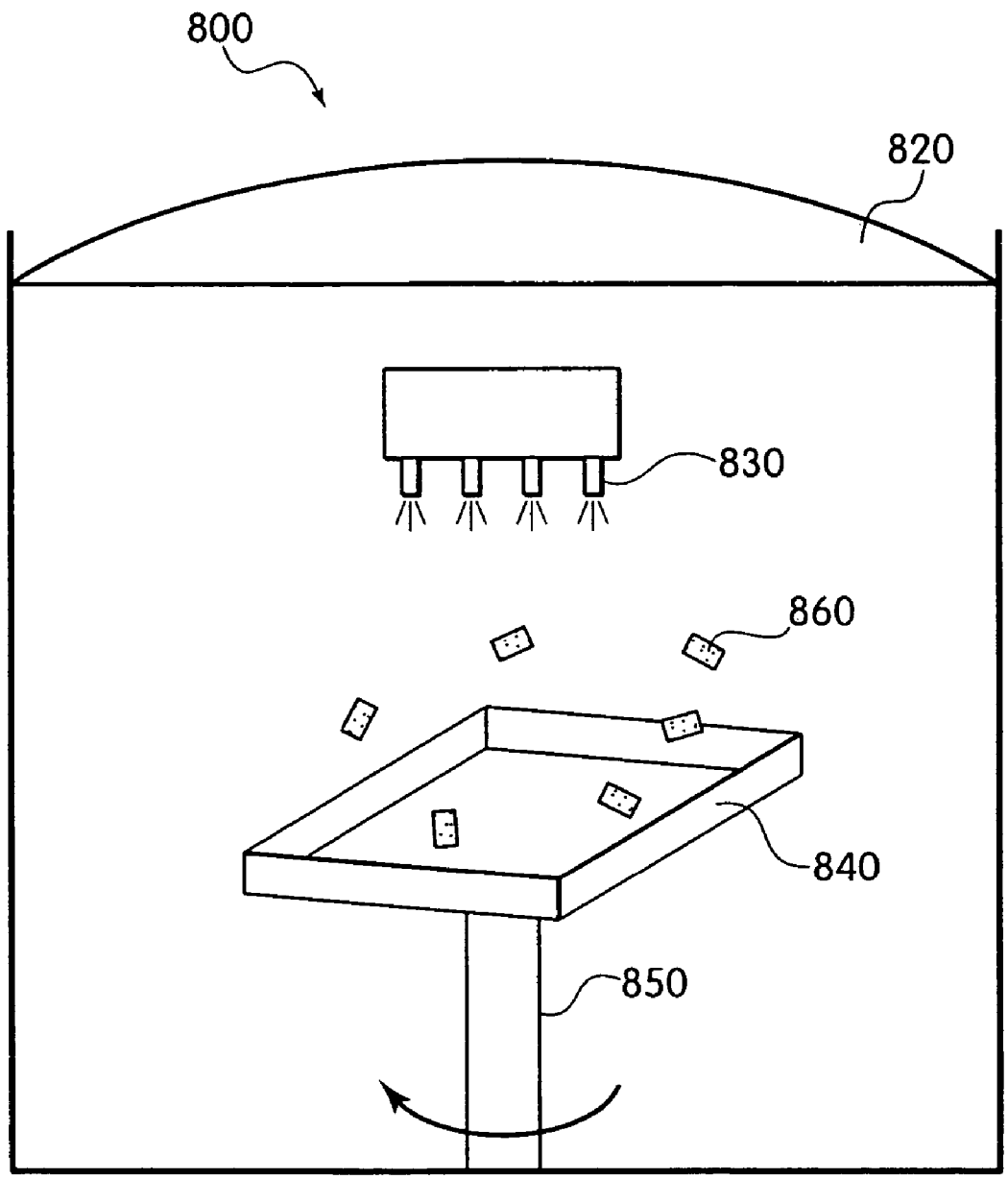
FIG. 8 illustrates a vibrating rotating container coating apparatus in accordance with another embodiment of the present invention.

FIG. 8 shows another embodiment of the present invention. In FIG. 8, coating device 800 can be clearly seen. In this embodiment, medical devices 860 may be placed within a vibrating container 840, which is also rotated either clockwise or counterclockwise by an attached rotating structure 850. In this embodiment the suspension of the medical devices 860 is due both to the vibrations of the vibrating container 840, as well as the rotational movement of the vibrating container 840. As the medical devices 860 are suspended above the vibrating container 840, they can be coated with coating material provided through coating nozzles 830. Any coating material not adhered to the medical devices 860 can be exhausted through exhaust 820. Also, as noted above, the coating nozzles are not uniformly spaced about the coating chamber but are, instead, ganged together in a position above the vibrating structure 840.

Figure 9:
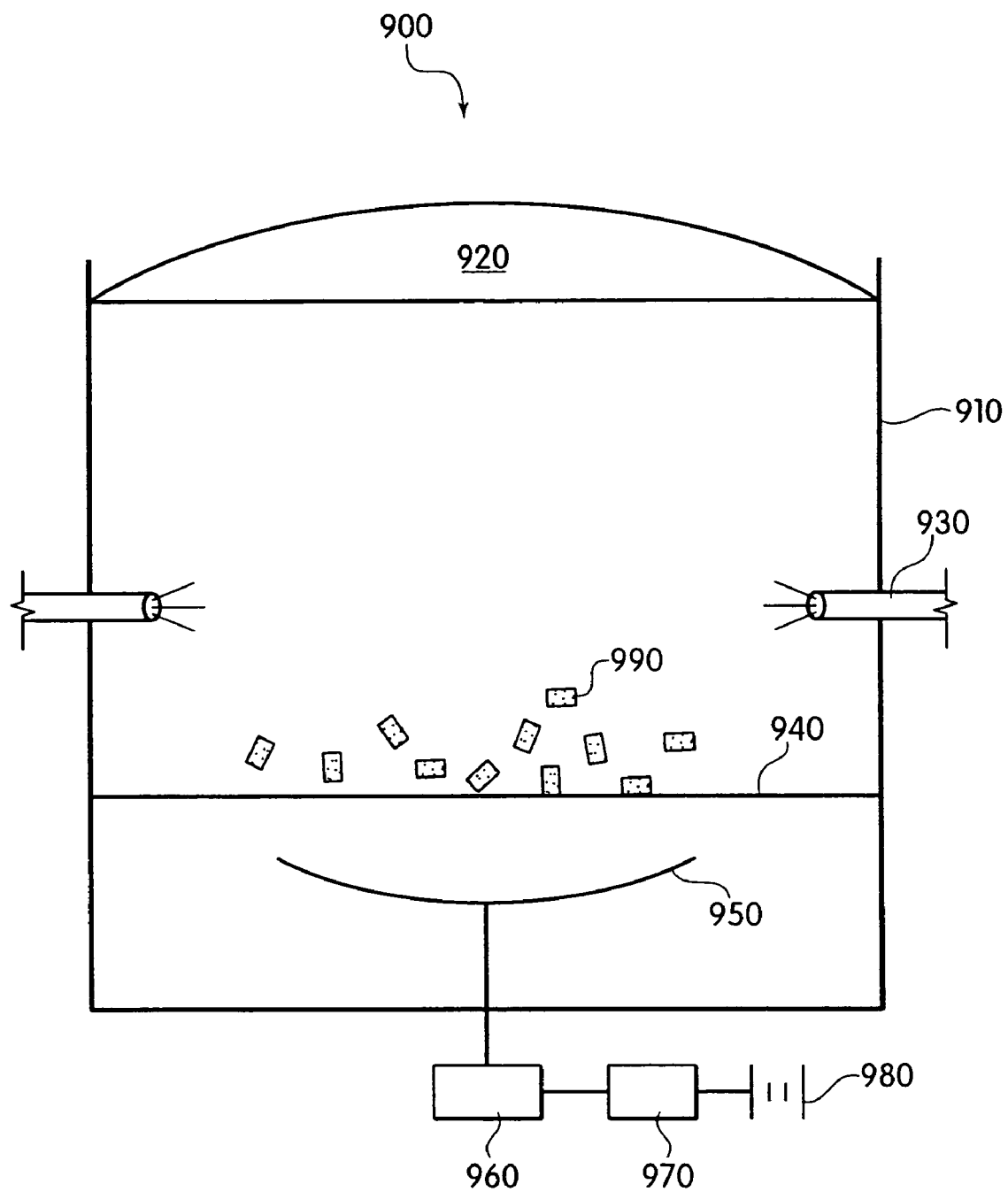
FIG. 9 illustrates an acoustical coating apparatus in accordance with another embodiment of the present invention.

FIG. 9 shows yet another embodiment of the present invention. In this embodiment, device 900 uses acoustical means to suspend medical devices 990 during coating. In device 900, medical devices 990 can be placed on a mesh or other screening device 940 within the coating container 910. Then, during the coating process, these medical devices 990 may be urged upwards by the pressure waves generated from acoustical vibrating structure or diaphram 950 located below the mesh 940. This acoustical diaphram may be attached to a driver 960, which is in turn attached to a frequency generator 970 and a power source 980. The frequency driver 960 in this embodiment may send a signal to the vibrating structure or diaphragm 950, thereby causing it to vibrate. This signal may be both cyclical, at a predetermined frequency, and random. As a result of the vibrations of diaphragm 950, the air above the diaphragm moves and, when containing enough energy, forces the medical devices 990 away from the mesh or screen 940.

As the medical devices 990 are suspended above the mesh or screen all of their surfaces may become exposed to and thereby coated by the coating material being introduced by the coating nozzles 930. Any coating material not adhered to the medical devices 990 can be exhausted through exhaust 920.

The medical devices that may be coated through any of these embodiments include stents, medical balloons, grafts, vena-cava filters, combinations thereof, as well as any other device that may benefit from a coating. Furthermore, these medical devices can be coated one at a time as well as in groups. They may also be coated continuously or by a batch process.

The coatings being applied can include numerous available coatings and may be both single and multi-layered. When multiple layers are being applied it may be preferable to dry the coatings between each coat. Moreover, in addition to drying, the coating layers can also be cured. As used herein, drying refers to the driving off of a solvent from the coating material and curing refers to crosslinking, initiating a chemical reaction at ambient or with heat, conditioning, heating, or combinations thereof, the coating materials.

Other variations on these embodiments are also plausible. For instance, the belt of the conveyor belt can be made with any number of different materials, including rubber. Moreover, it may be either a solid or perforated, as in a mesh. Likewise, the rotating container can include any structure that will hold the medical devices both as they are vibrated and rotated. For example, a modified pan coater would suffice. Furthermore, the vibrating plate can itself be made of any suitable material, and can also be solid or perforated. In each case, it is preferable that the vibrating structure is configured such that the medical devices do not vibrate off the structure or through the structure.

In addition to the mechanical and acoustical means described above, other embodiments of the present invention can include one or more gas flow structures. The gas flow structures helping to suspend the medical devices, move the medical devices into and out of the coating chamber or both. Examples of gases that may be employed include air, nitrogen, oxygen, carbon dioxide, and any of the inert gases. Moreover, in another embodiment, the medical devices may be surrounded by protective devices in order to ensure that one medical device does not interfere with another medical device.

Still further, rather than having a separate vibrating structure within the coating chamber the coating chamber itself may vibrate to lift the medical devices into the air.

Examples of various embodiments of the present invention are described and provided below.

EXAMPLE 1

Coronary stents are coated with a polymeric coating solution in accordance with the present invention.

Numerous (approximately 300 to 600 in this example) NIR stents (Medinol, Tel Aviv) are placed in a Wurster fluidized bed chamber, such as a GPCG-1 (available from Glatt Air Techniques, Ramsey N.J.). The stents are each about 9 mm-32 mm in length, about 1.5 mm-3.0 mm in diameter, about 7 mg-35 mg in weight, and about 46-200 $mm.sup.2$ in surface area.

A coating solution of polyurethane is prepared by mixing the following components (in approximate weight percentages): 0.5-1.0% Corethane 50D (Corvita, Miami, Fla.), 1.0-10.0% dimethylacetamide, and balance tetrahydrofuran. The solution components are mixed using a magnetic stirrer for at least about 8 hours to form a solution or dispersion, which is thereafter filtered with a 1.0 micron Teflon filter.

The stents are suspended using fluidizing air at about 2-20 psi, at a temperature of about 20-90C. and a dew point of about 10-60C. The stents are coated by pumping about 100-400 gm of the coating solution at about 0.1-6 ml/min to a nozzle located at the center of the perforated plate. The coating solution is atomized with compressed atomizing air operating at a pressure of about 2-40 psi and a flow rate of about 5 cfm. The atomizing air has a temperature of about 10-60° C. and a dew point of about 0-40° C.

Coating of the suspended stents continues until all of the coating solution has been pumped through the nozzle. Following the coating process, the stents are continued to be suspended for about 5-180 minutes to allow for the polymer coating layer to completely dry. After drying, the stents are removed from the Wurster fluidization chamber.

Because the stents are suspended in an air stream during the coating process, the coated stents do not display surface defects that normally result when a stent is held during coating. In addition, this is a batch process in which each stent is exposed to identical process conditions. The coating thickness depends on the size of the stent and the amount of the coating solution applied. As a result of the good control over processing parameters during coating, the coating on each stent strut is substantially identical.

EXAMPLE 2

Coronary stents are coated with a layer that comprises both polymeric and drug coating materials in accordance with the present invention.

NIR® stents are placed in a Wurster fluidized bed chamber, as described in Example 1. A coating solution is prepared by mixing the following components (in approximate weight percentages): about 0.5-2.0% Elvax 40W (available from Dupont, Wilmington, Del.), about 0.05-0.6% paclitaxel, balance chloroform. The coating solution components are mixed with a magnetic stirrer for at least 8 hours to form a solution or dispersion, which is thereafter filtered with a 0.2 micron Teflon® filter.

The stents are suspended and coated by the processing parameters described in Example 1. The coating process results in stents coated with uniform coating layers in which paclitaxel is evenly distributed on each stent and substantially the same dose applied to every stent in the batch.

EXAMPLE 3

Coronary stents are coated with multiple polymer coating layers in sequence distributed on each stent and the same dose applied to every stent in the batch in accordance with the present invention.

NIR® stents are placed in a Wurster fluidized bed chamber, as described in Example 1. A primer coating solution is prepared by mixing the following components (in approximate weight percentages): 0.01-2% Ultrathene UE631-04 (Equistar Chemical, LP, Houston, Tex.) and 99% Chloroform. The stents are suspended and coated by the processing parameters described in Example 1. When the primer coating is completely dry, the stents are further coated with a topcoat solution comprising (in approximate weight percentages): 0.5-0.65% Corethane 50D polyurethane, 1.0-10.0% dimethylacetamide, and balance tetrahydrofuran, prepared by the process described in Example 1.

The coating process results in stents having uniform, dual-layered coatings. The application of the primer coating enhances the adhesion of the topcoat layer to the stents. In addition, by applying several layers in sequence without removing the stents from the fluidization chamber, exposure of the stents to an outside environment between layers is minimized.

EXAMPLE 4

As a variation to Example 2, a barrier layer is applied to the stents coated with a polymer/drug layer in accordance with the present invention. A barrier layer of ethylene vinyl acetate copolymer or silicone protects the underlying polymer/drug layer from atmospheric degradation such as by oxidative or hydrolytic breakdown. The barrier layer also preferably improves abrasion resistance and durability, or may be used to control the start or rate of release of the drug from the underlying polymer/drug layer in vivo.

The barrier layer is the same or different composition as the polymer in the polymer/drug layer. For example, the barrier layer optionally comprises a dilution of MED-6605 (Nusil Silicone Technology, Carpinteria, Calif.) to 1% solids using chloroform. The hydrophobic silicone barrier reduces the release rate from the polyurethane/paclitaxel layer. Coating of both the barrier layer and polymer/drug layer is preferably conducted in sequence without removing the stents from the fluidization chamber.

The release profile of the drug may also be altered by concurrently applying several layers of gradient concentrations to yield a multi-phasic release profile. For example, the ratio of copolymers of polylactic acid ("PLA") and polyglycolic acid ("PGA") (Birmingham Polymers, Birmingham, Ala.) containing 0.1-10% of a peptide analog such as an analog of Somatostatin may be varied sequentially so that the drug has multiple peak release drug concentrations. For example, the initial coated layer may comprise PLA with drug, followed by 85:15 DL-PLG with drug, followed by 75:25 DL-PGA followed by 65:35 DL-PLG and 50:50 DL-PLG with drug, and so on. The release rate from each layer is optionally different such that the final result is several different peaks corresponding to the release from each individual layer. Layers are not limited to a single drug.

EXAMPLE 5

The invention includes the sequential application of several layers that contain components that are incompatible or do not share a common solvent system. For example, an initial coating layer applied to a medical device may contain paclitaxel and corethane polyurethane coated from solutions containing dimethylacetamide and tetrahydrofuran. A second coating layer may comprise an aqueous-based coating formulation containing agents that enhance surface biocompatibility such as heparin or albumin. For example, paclitaxel-PU is applied as a solution in dimethyl acetamide as a first layer, followed by application of heparin and/or polyethyleneglycol in aqueous solution as a second layer. As yet another example, benzalkonium chloride (a cationic surface-active agent) is applied as a first layer, followed by heparin (an anionic biocompatible polysaccharide) as a second layer, thus forming an ionic bond.

The invention includes parallel applications of drug(1)-solvent(1) and polymer(1)-solvent(2), where the: drug and polymer are soluble in different solvents or are incompatible or unstable when present together. As an example, the invention is used for the simultaneous application of aqueous solution of doxorubicin hydrochloride and silicone polymer in tetrahydrofuran from two separate feeds, wherein the latter is used to form a drug-matrix in situ and to control release kinetics. As another example, DNA solution is simultaneously applied with cationic lipid systems from two separate feeds to eliminate shelf-life stability issues associated with DNA-lipid complex formulations that exhibit undesirable increases in size and turbidity as a function of salt concentration.

The invention includes parallel applications of drug(1)-polymer(1)-solvent(1) and drug(2)-polymer(2)-solvent(2) to eliminate compatibility or solubility issues. Examples include the simultaneous application of (i) cisplatin-hydroxypropyl methyl cellulose-water and paclitaxel-PCL/PLA-chloroform from two different feeds; (ii) albumin or gelatin solution from one feed and glutareldehyde crosslinker from second feed; and (iii) acrylate monomer solution from one feed and methylene bis acrylamide as crosslinker for the second feed.

The simultaneous coating of medical devices with incompatible coating materials is carried out, for example, by introducing separate feed streams into a coating chamber via separate nozzles. When compared to conventional coating techniques such as dip coating and spray coating, this embodiment of the invention substantially expands the number of coating formulations and combinations of polymers and drugs that may be coated onto medical devices. For example, an aqueous-based solution containing a desired therapeutic substance is atomized simultaneously with a solvent-based polymer coating solution.

EXAMPLE 6

The invention includes the coating of medical devices with coating materials from low-viscosity aqueous or non-aqueous solutions that would otherwise be difficult to achieve via dip-coating or spray coating applications. For example, peptide and protein drugs, which often undergo denaturation in the presence of organic solvents or excessive heat, are easily coated onto medical devices in accordance with the present invention. In such applications, the drug is applied from an aqueous formulation and the coating process is controlled (i.e, in terms of temperature and humidity) to minimize drug degradation. As another example, low viscosity solutions of RGD peptides or phosphorylcholines are deposited as monolayers or as thicker coatings for use as drug delivery depots.

The present invention provides devices and methods for coating medical devices while the medical devices are suspended. Although the present invention has been described with respect to several exemplary embodiments, there are many other variations of the above-described embodiments, which will be apparent to those skilled in the art, even where elements have not explicitly been designated as exemplary. It is understood that these modifications are within the teaching of the present invention, which is further defined by the claims appended hereto.

What is claimed is:

1. A coating system comprising:
a coating chamber;
a cage for supporting a medical device to be coated, the cage positioned in the coating chamber;
a vibration source having a diaphragm exposed to the coating chamber, the vibration source configured to generate pressure waves sufficient to suspend the cage positioned in the coating chamber above the vibration source without the vibration source contacting the cage; and
a coating source, the coating source positioned to introduce coating into the coating chamber
wherein the vibration source is positioned below a screen and wherein the source of coating contains a therapeutic.

2. The system of claim 1 further comprising a coating filter coupled to the coating chamber.

3. The system of claim 1 wherein the vibration source is exposed to the coating chamber.

4. The system of claim 1 wherein the coating source contains a coating that covers a surface of a medical device positioned in the coating chamber after the medical device is removed from the coating chamber.

5. The system of claim 1 wherein the coating chamber contains a medical device.

6. The system of claim 5 wherein the medical device is a stent.

7. The system of claim 1 wherein the coating chamber contains a plurality of medical devices.

8. A coating system comprising:
a coating chamber;
a cage for supporting a medical device to be coated, the cage positioned in the coating chamber;
a vibration source having a diaphragm exposed to the coating chamber, the vibration source configured to generate pressure waves sufficient to suspend the cage positioned in the coating chamber above the vibration source without the vibration source contacting the cage; and
a coating source, the coating source positioned to introduce coating into the coating chamber wherein the coating source is positioned above a screen in the coating chamber.

9. An apparatus for coating a medical implant comprising:
a coating chamber;
a vibration source, the vibration source adapted to suspend an implantable medical device positioned in the coating chamber above the vibration source; and
a coating source, the coating source configured to introduce coating into the coating chamber;
wherein the coating source includes a nozzle coupled to a supply of coating,
wherein the vibration source has a vibrating structure positioned within the coating chamber, the vibrating structure having an exposed side, wherein the exposed side has a space between it and the coating chamber and
wherein the nozzle is positioned beneath the vibrating structure.

10. An apparatus for coating a medical implant comprising:
a coating area adapted to receive medical implants for implantation within the body of a patient;
means for supplying a therapeutic coating into the coating area; and means for suspending the medical implants in the coating area during the coating process;

wherein the means for suspending the medical implants in the coating area during the coating process comprises a vibration structure and a nozzle, and wherein the vibrating structure has an exposed side, wherein the exposed side has a space between it and the coating area.

* * * * *